US012558362B2

(12) United States Patent　　　(10) Patent No.: US 12,558,362 B2
Checketts et al.　　　　　　　　　(45) Date of Patent: Feb. 24, 2026

---

(54) USE OF CANNABIDIOL IN THE TREATMENT OF SEIZURES ASSOCIATED WITH RETT SYNDROME

(71) Applicant: JAZZ PHARMACEUTICALS RESEARCH UK LIMITED, Sittingbourne (GB)

(72) Inventors: Daniel Adam Checketts, Cambridgeshire (GB); Kevin James Craig, Cambridgeshire (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 314 days.

(21) Appl. No.: 18/006,127

(22) PCT Filed: Jul. 15, 2021

(86) PCT No.: PCT/EP2021/069870
§ 371 (c)(1),
(2) Date: Jan. 19, 2023

(87) PCT Pub. No.: WO2022/017937
PCT Pub. Date: Jan. 27, 2022

(65) Prior Publication Data
US 2023/0285427 A1　　Sep. 14, 2023

(30) Foreign Application Priority Data
Jul. 20, 2020　(GB) ..................................... 2011174

(51) Int. Cl.
| *A61K 31/65* | (2006.01) |
| *A61K 31/00* | (2006.01) |
| *A61K 45/06* | (2006.01) |
| *A61P 25/08* | (2006.01) |

(52) U.S. Cl.
CPC ............ *A61K 31/658* (2023.05); *A61K 45/06* (2013.01); *A61P 25/08* (2018.01)

(58) Field of Classification Search
CPC ...................................................... A61K 31/65
USPC ........................................................ 514/732
See application file for complete search history.

(56) References Cited

U.S. PATENT DOCUMENTS

| 8,632,825 | B2 | 1/2014 | Velasco Diez et al. |
| 8,790,719 | B2 | 7/2014 | Parolaro et al. |
| 9,017,737 | B2 | 4/2015 | Kikuchi et al. |
| 9,125,859 | B2 | 9/2015 | Whalley et al. |
| 9,474,726 | B2 | 10/2016 | Guy et al. |
| 9,949,936 | B2 | 4/2018 | Guy et al. |
| 9,949,937 | B2 | 4/2018 | Guy et al. |
| 9,956,183 | B2 | 5/2018 | Guy et al. |
| 9,956,184 | B2 | 5/2018 | Guy et al. |
| 9,956,185 | B2 | 5/2018 | Guy et al. |
| 9,956,186 | B2 | 5/2018 | Guy et al. |
| 10,092,525 | B2 | 10/2018 | Guy et al. |
| 10,111,840 | B2 | 10/2018 | Guy et al. |
| 10,137,095 | B2 | 11/2018 | Guy et al. |
| 10,583,096 | B2 | 3/2020 | Guy et al. |
| 10,603,288 | B2 | 3/2020 | Guy et al. |
| 10,709,671 | B2 | 7/2020 | Guy et al. |
| 10,709,673 | B2 | 7/2020 | Guy |
| 10,709,674 | B2 | 7/2020 | Guy et al. |
| 10,765,643 | B2 | 9/2020 | Guy et al. |
| 10,807,777 | B2 | 10/2020 | Whittle |
| 10,849,860 | B2 | 12/2020 | Guy et al. |
| 10,918,608 | B2 | 2/2021 | Guy et al. |
| 10,966,939 | B2 | 4/2021 | Guy et al. |
| 11,065,209 | B2 | 7/2021 | Guy et al. |
| 11,065,227 | B2 | 7/2021 | Stott et al. |
| 11,096,905 | B2 | 8/2021 | Guy et al. |
| 11,147,776 | B2 | 10/2021 | Stott et al. |
| 11,147,783 | B2 | 10/2021 | Stott et al. |
| 11,154,516 | B2 | 10/2021 | Guy et al. |
| 11,154,517 | B2 | 10/2021 | Guy et al. |
| 11,160,757 | B1 | 11/2021 | Wilkhu et al. |
| 11,160,795 | B2 | 11/2021 | Guy et al. |
| 11,207,292 | B2 | 12/2021 | Guy et al. |
| 11,229,612 | B2 | 1/2022 | Wright et al. |
| 11,291,631 | B2 | 4/2022 | Shah |
| 11,311,498 | B2 | 4/2022 | Guy et al. |
| 11,357,741 | B2 | 6/2022 | Guy et al. |
| 11,400,055 | B2 | 8/2022 | Guy et al. |

(Continued)

FOREIGN PATENT DOCUMENTS

| EP | 2311475 A2 | 4/2011 |
| GB | 2487183 A | 7/2012 |

(Continued)

OTHER PUBLICATIONS

Amada, N. et al., "Cannabidivarin (CBDV) suppresses pentylenetetrazole (PTZ)-induced increases in epilepsy-related gene expression," 2013, PeerJ, 1:e214; 18 pages; http://dx.doi.org/10.7717/peerj.214.

Clinical Trials.Gov [online], Identifier: NCT03848832, Efficacy and Safety of Cannabidiol Oral Solution (GWP42003-P, CBD-OS) in Patients With Rett Syndrome (ARCH), Jazz Pharmaceuticals, U.S. National Library of Medicine, last update posted Sep. 2, 2022, 8 pages; Retrieved from https://clinicaltrials.gov/ct2/show/NCT03848832.

Eadie, Shortcomings in the current treatment of epilepsy, Expert Rev Neurother, 12(12):1419-1427 (2012).

Elsohly, M. & Gul, W., Handbook of Cannabis, Chapter 1, Constituents of Cannabis Sativa, Roger Pertwee, Ed., 2012, 21 pages.

(Continued)

*Primary Examiner* — Raymond J Henley, III
(74) *Attorney, Agent, or Firm* — COOLEY LLP

(57) ABSTRACT

The present invention relates to the use of cannabidiol (CBD) for the treatment of seizures associated with rare epilepsy syndromes. In particular the seizures associated with rare epilepsy syndromes that are treated are those which are experienced inpatients diagnosed with Rett syndrome. In a further embodiment the types of seizures include tonic, tonic-clonic, absence seizures and focal seizures with impairment. Preferably the dose of CBD is between 5 mg/kg/day to 50 mg/kg/day.

13 Claims, No Drawings

(56) References Cited

U.S. PATENT DOCUMENTS

| | | |
|---|---|---|
| 11,406,623 B2 | 8/2022 | Guy et al. |
| 11,419,829 B2 | 8/2022 | Whalley et al. |
| 11,426,362 B2 | 8/2022 | Wright et al. |
| 11,446,258 B2 | 9/2022 | Guy et al. |
| 11,590,087 B2 | 2/2023 | Guy et al. |
| 11,633,369 B2 | 4/2023 | Guy et al. |
| 2015/0359756 A1 | 12/2015 | Guy et al. |
| 2017/0239193 A1 | 8/2017 | Guy et al. |
| 2017/0349517 A1 | 12/2017 | Dickman et al. |
| 2018/0071210 A1 | 3/2018 | Wilkhu et al. |
| 2018/0228751 A1 | 8/2018 | Stott et al. |
| 2019/0167583 A1 | 6/2019 | Shah |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0169824 A1 | 6/2021 | Guy et al. |
| 2021/0177773 A1 | 6/2021 | Guy et al. |
| 2021/0290565 A1 | 9/2021 | Guy et al. |
| 2021/0330636 A1 | 10/2021 | Guy et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0087951 A1 | 3/2022 | Knappertz |
| 2022/0096397 A1 | 3/2022 | Wright et al. |
| 2022/0168266 A1 | 6/2022 | Guy et al. |
| 2022/0183997 A1 | 6/2022 | Guy et al. |
| 2022/0184000 A1 | 6/2022 | Guy et al. |
| 2022/0202738 A1 | 6/2022 | Guy et al. |
| 2022/0211629 A1 | 7/2022 | Wilkhu et al. |
| 2022/0226257 A1 | 7/2022 | Guy et al. |
| 2022/0233495 A1 | 7/2022 | Silcock et al. |
| 2022/0249396 A1 | 8/2022 | Guy et al. |
| 2022/0257529 A1 | 8/2022 | Guy et al. |
| 2022/0265573 A1 | 8/2022 | Guy et al. |
| 2022/0288055 A1 | 9/2022 | Silcock et al. |
| 2022/0378714 A1 | 12/2022 | Guy et al. |
| 2022/0387350 A1 | 12/2022 | Guy et al. |
| 2022/0395471 A1 | 12/2022 | Guy et al. |
| 2023/0000789 A1 | 1/2023 | Guy et al. |
| 2023/0022487 A1 | 1/2023 | Guy et al. |
| 2023/0024312 A1 | 1/2023 | Whalley et al. |
| 2023/0026079 A1 | 1/2023 | Guy et al. |
| 2023/0032502 A1 | 2/2023 | Guy et al. |
| 2023/0038423 A1 | 2/2023 | Silcock et al. |
| 2023/0068885 A1 | 3/2023 | Guy et al. |
| 2023/0143812 A1 | 5/2023 | Knappertz et al. |
| 2023/0235825 A1 | 7/2023 | Thompson et al. |
| 2023/0248664 A1 | 8/2023 | Guy |
| 2023/0263744 A1 | 8/2023 | Guy |
| 2023/0277560 A1 | 9/2023 | Checketts et al. |
| 2023/0277561 A1 | 9/2023 | Checketts et al. |
| 2023/0277562 A1 | 9/2023 | Checketts et al. |
| 2023/0277563 A1 | 9/2023 | Checketts et al. |
| 2023/0285419 A1 | 9/2023 | Checketts et al. |
| 2023/0285420 A1 | 9/2023 | Checketts et al. |
| 2023/0285421 A1 | 9/2023 | Checketts et al. |
| 2023/0285422 A1 | 9/2023 | Checketts et al. |
| 2023/0285423 A1 | 9/2023 | Checketts et al. |
| 2023/0285424 A1 | 9/2023 | Checketts et al. |
| 2023/0285425 A1 | 9/2023 | Checketts et al. |
| 2023/0285426 A1 | 9/2023 | Checketts et al. |
| 2023/0285428 A1 | 9/2023 | Checketts et al. |
| 2023/0301934 A1 | 9/2023 | Whalley et al. |
| 2023/0301936 A1 | 9/2023 | Guy et al. |
| 2023/0310464 A1 | 10/2023 | Checketts et al. |
| 2023/0346809 A1 | 11/2023 | Craig |
| 2023/0372367 A1 | 11/2023 | Checketts et al. |
| 2023/0372368 A1 | 11/2023 | Checketts et al. |
| 2024/0016819 A1 | 1/2024 | Craig |
| 2024/0025858 A1 | 1/2024 | Silcock et al. |
| 2024/0033229 A1 | 2/2024 | Guy et al. |
| 2024/0033272 A1 | 2/2024 | Checketts et al. |
| 2024/0043388 A1 | 2/2024 | Silcock et al. |
| 2024/0050452 A1 | 2/2024 | Craig et al. |
| 2024/0091241 A1 | 3/2024 | Guy et al. |
| 2024/0130981 A1 | 4/2024 | Wilkhu |
| 2024/0131041 A1 | 4/2024 | Tse |
| 2024/0165048 A1 | 5/2024 | Guy |
| 2024/0207220 A1 | 6/2024 | Guy et al. |
| 2024/0215910 A1 | 7/2024 | Tse et al. |
| 2024/0226032 A9 | 7/2024 | Wilkhu et al. |
| 2024/0226123 A9 | 7/2024 | Tse |
| 2024/0238218 A1 | 7/2024 | Silcock et al. |
| 2024/0254066 A1 | 8/2024 | Silcock et al. |
| 2024/0254072 A1 | 8/2024 | Silcock et al. |
| 2024/0261234 A1 | 8/2024 | Guy |
| 2024/0293762 A1 | 9/2024 | Loft et al. |

FOREIGN PATENT DOCUMENTS

| | | |
|---|---|---|
| GB | 2539472 A | 12/2016 |
| GB | 2542797 A | 4/2017 |
| GB | 2569961 A | 7/2019 |
| WO | WO-2011121351 A1 | 10/2011 |
| WO | WO-2015193667 A1 | 12/2015 |
| WO | WO-2015193668 A1 | 12/2015 |
| WO | WO-2016094810 A2 | 6/2016 |
| WO | WO-2016203239 A1 | 12/2016 |
| WO | WO-2017178807 A1 | 10/2017 |
| WO | WO-2018061007 A1 | 4/2018 |
| WO | WO-2018205022 A1 | 11/2018 |
| WO | WO-2019135075 A1 | 7/2019 |
| WO | WO-2019207319 A1 | 10/2019 |
| WO | WO-2020105005 A1 | 5/2020 |
| WO | WO-2020112460 A1 | 6/2020 |
| WO | WO-2021079148 A1 | 4/2021 |

OTHER PUBLICATIONS

European Medicines Agency, Public summary of opinion on orphan designation, Cannabidivarin for the treatment of Rett syndrome, Jan. 5, 2018, 4 pages; www.ema.europa.eu/contact.

Gaoni, Y. & Mechoulam, R., "Isolation, Structure, and Partial Synthesis of an Active Constituent of Hashish," J. Am. Chern. Soc. 1964, 86, 8, 1646-1647.

Gaoni, Y. & Mechoulam, R., "The Isolation and Structure of Δ1-Tetrahydrocannabinol and Other Neutral Cannabinoids from Hashish," J Am Chern Soc. Jan. 13, 1971;93(1):217-24. doi: 10.1021/ja00730a036.

Guidance for Industry, Botanical Drug Development, U.S. Department of Health and Human Services, Food and Drug Administration, Center for Drug Evaluation and Research (CDER); Dec. 2016, Pharmaceutical Quality/CMC, 34 pages; https://www.fda.gov/media/93113/download.

Hill, "Cannabidivarin-rich cannabis extracts are anticonvulsant in mouse and rat via a CB 1 receptor-independent mechanism," British Journal of Pharmacology, 170(3): 679-692 (2013).

Hill et al., "Cannabidivarin is anticonvulsant in mouse and rat," Br J Pharmacol, 167(8):1629-1642 (2012).

Huizenga, M. N. et al., Preclinical safety and efficacy of cannabidivarin for early life seizures, Neuropharmacology. Apr. 2019 ; 148: 189-198. doi:10.1016/j.neuropharm.2019.01.002.

Kwan et al., Definition of drug resistant epilepsy: consensus proposal by the ad hoc Task Force of the ILAE Commission on Therapeutic Strategies, Epilepsia. Jun. 2010;51(6):1069-77.doi:10.

(56)  References Cited

OTHER PUBLICATIONS

1111/j.1528-1167.2009.02397.x. Epub Nov. 3, 2009. Erratum in: Epilepsia. Sep. 2010; 51(9):1922.

Lewis, M. M. et al., Chemical Profiling of Medical Cannabis Extracts, ACS Omega, 2:6091-9103, 2017; doi:10.1021/acsomega. 7b00996.

Mouro, F. M. et al., From Cannabinoids and Neurosteroids to Statins and the Ketogenic Diet: New Therapeutic Avenues in Rett Syndrome?, Frontiers in Neuroscience, vol. 13, Article 680, Jul. 2019, 22 pages; https://www.frontiersin.org/articles/10.3389/fnins.2019. 00680/full.

Sands, T. et al., Long-Term Safety, Tolerability, and Efficacy of Cannabidiol in Children with Refractory Epilepsy: Results from an Expanded Access Program in the US, CNS Drugs, 33:47-60 (2019).

Schafroth, M. A. et al., "Sterodivergent Total Synthesis of Δ9-Tetrahydrocannabinols," Angew. Chem. Int. Ed., 53:13898-13901 (2014).

Smith, R. M. & Kempfert, K. D., "Δ1-3,4-C/S-Tetrahydrocannabinol in Cannabis Sativa," Phytochemistry, 16:1088-1089 (1977).

Sulak, D. et al., The current status of artisanal cannabis for the treatment of epilepsy in the United States, Epilepsy & Behavior, 70:328-333 (2017).

Thurman et al., "Standards for epidemiologic studies and surveillance of epilepsy," Epilepsia, 52 (Suppl 7):2-26 (2011).

Trost, B. M. & Dogra, K., "Synthesis of (-)-Δ9-trans-Tetrahydrocannabinol: Stereocontrol via Mo-Catalyzed Asymmetric Allylic Alkylation Reaction," Organic Letters, 9(5):861-863 (2007).

Vigli, D. et al., Chronic treatment with the phytocannabinoid Cannabidivarin (CBDV) rescues behavioural alterations and brain atrophy in a mouse model of Rett syndrome, Neuropharmacology, 140:121-129 (2018).

Way, K., How One Canna-Mom Treats Her Daughter's Rett Syndrome With Cannabis, 2023, https://cannabisnow.com/how-one-canna-mom-treats-her-daughters-rett-syndrome-with-cannabis/, 15 pages.

Zamberletti, E. et al., Cannabidivarin completely rescues cognitive deficits and delays neurological and motor defects in male Mecp2 mutant mice, Journal of Psychopharmacology, 2019, vol. 33(7) 894-907; https://doi.org/10.1177/0269881119844184.

Harvey, D. J., "Characterization of the Butyl Homologues of Delta1-tetrahydrocannabinol, Cannabinol and Cannabidiol in Samples of Cannabis by Combined Gas Chromatography and Mass Spectrometry," J. Pharm. Pharmac., 28:280-285 (1976).

Morales, P. et al., "An Overview on Medicinal Chemistry of Synthetic and Natural Derivatives of Cannabidiol," Frontiers in Pharmacology, 8:422 (2017); doi:10.3389/fphar.2017.00422, 18 pages.

clinical trials.gov [online], Identifier: NCT03202303, Cannabidivarin (CBVD) vs. Placebo in Children With Autism Spectrum Disorder (ASD), Montefiore Medical Center, National Center for Biotechnology, last update posted Aug. 21, 2024, [retrieval date unknown], 11 pages; Retrieved from https://clinicaltrials.gov/study/NCT03202303?term=NCT03202303&viewType=Table&rank=1&tab=history.

EPIDIOLEX (cannabidiol) oral solution, CV, Prescribing Information, 2018, [retrieval date unknown], 30 pages; https://www.accessdata. fda.gov/drugsatfda_docs/label/2018/210365lbl.pdf.

Pertwee, R. G., "The Pharmacology and Therapeutic Potential of Cannabidiol," Cannabinoids, Chapter 3, DiMarzo, V. (Ed.), pp. 32-83 (2004).

Takahashi, S., "Understanding the pathogenesis of Rett syndrome—Clinical features associated with mutations in the causative genes (MECP2, CDKL5, FOXG1), " Brain and Development, 46:117-20 (2014), with English translation, 13 pages.

1

USE OF CANNABIDIOL IN THE TREATMENT OF SEIZURES ASSOCIATED WITH RETT SYNDROME

CROSS-REFERENCE TO RELATED APPLICATIONS

This application is a U.S. National Phase application, filed under 35 U.S.C. § 371 (c), of International Application No. PCT/EP2021/069870, filed Jul. 15, 2021, which claims priority to, and the benefit of, United Kingdom Application No. 2011174.6, filed Jul. 20, 2020. Each of these documents is incorporated by reference herein in its entirety for all purposes.

FIELD OF THE INVENTION

The present invention relates to the use of cannabidiol (CBD) for the treatment of seizures associated with rare epilepsy syndromes. In particular the seizures associated with rare epilepsy syndromes that are treated are those which are experienced in patients diagnosed with Rett syndrome. In a further embodiment the types of seizures include tonic, tonic-clonic, absence seizures and focal seizures with impairment. Preferably the dose of CBD is between 5 mg/kg/day to 50 mg/kg/day.

In a further embodiment the CBD used is in the form of a highly purified extract of *cannabis* such that the CBD is present at greater than 95% of the total extract (w/w) and the cannabinoid tetrahydrocannabinol (THC) has been substantially removed, to a level of not more than 0.15% (w/w).

Preferably the CBD used is in the form of a botanically derived purified CBD which comprises greater than or equal to 98% (w/w) CBD and less than or equal to 2% (w/w) of other cannabinoids. More preferably the other cannabinoids present are THC at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w). The botanically derived purified CBD preferably also comprises a mixture of both trans-THC and cis-THC. Alternatively, a synthetically produced CBD is used.

Most preferably the other cannabinoids present are THC at a concentration of about 0.01% to about 0.1% (w/w); CBD-C1 at a concentration of about 0.1% to about 0.15% (w/w); CBDV at a concentration of about 0.2% to about 0.8% (w/w); and CBD-C4 at a concentration of about 0.3% to about 0.4% (w/w). Most preferably still the THC is present at a concentration of about 0.02% to about 0.05% (w/w).

Where the CBD is given concomitantly with one or more other anti-epileptic drugs (AED), the CBD may be formulated for administration separately, sequentially or simultaneously with one or more AED or the combination may be provided in a single dosage form.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as "failure of adequate trials of two tolerated and appropriately chosen and used AED schedules (whether as monotherapies or in combination) to achieve sustained seizure freedom" (Kwan et al., 2009).

Individuals who develop epilepsy during the first few years of life are often difficult to treat and as such are often termed treatment resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from an investigation into the type of seizures that the patient is experiencing is undertaken. Clinical observations and electroencephalography (EEG) tests are conducted and the type(s) of seizures are classified according to the ILEA classification.

Generalized seizures, where the seizure arises within and rapidly engages bilaterally distributed networks, can be split into six subtypes: tonic-clonic (grand mal) seizures; absence (petit mal) seizures; clonic seizures; tonic seizures; atonic seizures and myoclonic seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a bilateral convulsive seizure, which is the proposed terminology to replace secondary generalized seizures (generalized seizures that have evolved from focal seizures and are no longer remain localized).

Focal seizures where the subject's awareness/responsiveness is altered are referred to as focal seizures with impairment and focal seizures where the awareness or responsiveness of the subject is not impaired are referred to as focal seizures without impairment.

Rett syndrome is a brain disorder that occurs almost exclusively in girls. After birth, girls with Rett syndrome have 6 to 18 months of apparently normal development before developing severe problems with language and communication, learning, coordination, and other brain functions.

Early in childhood, affected girls lose purposeful use of their hands and begin making repeated hand wringing, washing, or clapping motions. They tend to grow more slowly than other children and about three-quarters have a small head size (microcephaly).

Other signs and symptoms that can develop include breathing abnormalities, spitting or drooling, unusual eye movements such as intense staring or excessive blinking, cold hands and feet, irritability, sleep disturbances, seizures, and an abnormal side-to-side curvature of the spine (scoliosis).

Nearly all cases of Rett syndrome are caused by a mutation in the methyl CpG binding protein 2, or MECP2 gene. The MECP2 gene contains instructions for the synthesis of a protein called methyl cytosine binding protein 2 (MeCP2), which is needed for brain development and acts as one of the many biochemical switches that can either increase gene expression or tell other genes when to turn off and stop producing their own unique proteins. Because theMECP2 gene does not function properly in individuals with Rett syndrome, insufficient amounts or structurally abnormal forms of the protein are produced and can cause other genes to be abnormally expressed.

Not everyone who has an MECP2 mutation has Rett syndrome. Mutations in the CDKL5 and FOXG 1 genes are also associated with Rett syndrome.

Cannabidiol (CBD), a non-psychoactive derivative from the *cannabis* plant, has demonstrated anti-convulsant properties in several anecdotal reports, pre-clinical and clinical studies both in animal models and humans. Three randomized control trials showed efficacy of the purified pharmaceutical formulation of CBD in patients with Dravet and Lennox-Gastaut syndrome.

Based on these three trials, a botanically derived purified CBD preparation was approved by FDA in June 2018 for the treatment of seizures associated with Dravet and Lennox-Gastaut syndromes.

A trial is currently underway to test the ability of botanically derived purified CBD in the treatment of behavioural symptoms associated with Rett syndrome[1]. It is not yet known whether CBD impacted any such symptoms.

In addition, the compound cannabidivarin (CBDV) has been found to rescue the behavioural alterations in a mouse model of Rett syndrome[2].

GB 2539472 discloses the use of highly purified CBD for the treatment of various types of seizures. However there is no data shown to suggest efficacy in the treatment of Rett syndrome.

An anecdotal report[1] discloses the treatment of a patient diagnosed with Rett syndrome with *cannabis* oil. The oil used was a full-spectrum *cannabis* oil, one that retains other compounds such as terpenes and flavonoids. It is further stated that the patient was dosed with a high-THC formulation.

A review by Mouro et al. (2019)[4] discusses different possible directions for future research for Rett syndrome, one of which includes the use of cannabinoids. The article however merely discusses this approach without providing any data of patients diagnosed with Rett syndrome who have successfully experienced a reduction in their seizures through the use of CBD.

Documents including WO 2020/105005 and WO 2020/112460 disclose the use of compounds such as fenfluramine to treat various epileptic syndromes, one of which listed is Rett syndrome. Whilst CBD in combination with fenfluramine is mentioned as a possible treatment, there is no data provided to support such a statement.

The applicant has found by way of an open label, expanded-access program that treatment with CBD resulted in a significant reduction in specific seizure types including tonic, tonic-clonic, absence seizures and focal seizures with impairment in patients diagnosed with Rett syndrome.

BRIEF SUMMARY OF THE DISCLOSURE

In accordance with a first aspect of the present invention there is provided a cannabidiol (CBD) preparation for use in the treatment of seizures associated with Rett syndrome.

In a further embodiment the seizures associated with Rett syndrome are tonic, tonic-clonic, absence seizures and focal seizures with impairment.

In a further embodiment, the CBD preparation comprises greater than 95% (w/w) CBD and not more than 0.15% (w/w) tetrahydrocannabinol (THC).

Preferably the CBD preparation comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC.

Preferably the CBD preparation is used in combination with one or more concomitant anti-epileptic drugs (AED).

Preferably the one or more AED is selected from the group consisting of: clobazam, levetiracetam, zonisamide, valproic acid, perampanel, clonazepam and diazepam.

In one embodiment the CBD is present is isolated from *cannabis* plant material. Preferably at least a portion of at least one of the cannabinoids present in the CBD preparation is isolated from *cannabis* plant material.

In a further embodiment the CBD is present as a synthetic preparation. Preferably at least a portion of at least one of the cannabinoids present in the CBD preparation is prepared synthetically.

Preferably the dose of CBD is greater than 5 mg/kg/day. More preferably the dose of CBD is 20 mg/kg/day. More preferably the dose of CBD is 25 mg/kg/day. More preferably the dose of CBD is 50 mg/kg/day.

In accordance with a second aspect of the present invention there is provided a method of treating seizures associated with Rett syndrome comprising administering a cannabidiol (CBD) preparation to the subject in need thereof.

DEFINITIONS

Definitions of some of the terms used to describe the invention are detailed below:

Over 100 different cannabinoids have been identified, see for example, Handbook of *Cannabis*, Roger Pertwee, Chapter 1, pages 3 to 15. These cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phytocannabinoids can be isolated from plants to produce a highly purified extract or can be reproduced synthetically.

"Highly purified cannabinoids" are defined as cannabinoids that have been extracted from the *cannabis* plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example, it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Tonic seizures" can be generalised onset, affecting both sides of the brain, or they can be focal onset, starting in just one side of the brain. If a tonic seizure starts in both sides of the brain, all muscles tighten and the subject's body goes stiff. If standing, they may fall to the floor, their neck may extend, eyes open wide and roll upwards, whilst their arms may raise upwards and legs stretch or contract. If a tonic seizure starts in one side of the brain muscles tighten in just one area of the body. Tonic seizures usually last less than one minute.

"Tonic-clonic seizures" consist of two phases: the tonic phase and the clonic phase. In the tonic phase the body becomes entire rigid, and in the clonic phase there is uncontrolled jerking. Tonic-clonic seizures may or may not be preceded by an aura, and are often followed by headache, confusion, and sleep. They may last mere seconds or continue for several minutes. These seizures are also known as a grand mal seizure.

"Absence seizures" also may be called "petit mal" seizures. These types of seizure cause a loss of awareness for a short time. They mainly affect children although can happen at any age. During an absence seizure, a person may: stare blankly into space; look like they are "daydreaming"; flutter their eyes; make slight jerking movements of their body or limbs. The seizures usually only last up to 15 seconds and may occur several times a day.

"Focal Seizures" are defined as seizures which originate within networks limited to only one hemisphere. What happens during the seizure depends on where in the brain the seizure happens and what that part of the brain normally does.

"Focal seizures with impairment" usually start in a small area of the temporal lobe or frontal lobe of the brain and involve other areas of the brain within the same hemisphere that affect alertness and awareness. Most subjects experience automatisms during a focal seizure with impaired consciousness.

DETAILED DESCRIPTION

Preparation Of Highly Purified CBD Extract

The following describes the production of the highly-purified (>95% w/w) cannabidiol extract which has a known and constant composition.

In summary the drug substance used is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD. Although the CBD is highly purified because it is produced from a *cannabis* plant rather than synthetically there is a small number of other cannabinoids which are co-produced and co-extracted with the CBD. Details of these cannabinoids and the quantities in which they are present in the medication are as described in Table A below.

TABLE A

| Composition of highly purified CBD extract | |
| --- | --- |
| Cannabinoid | Concentration |
| CBD | >95% w/w |
| CBDA | NMT 0.15% w/w |
| CBDV | NMT 1.0% w/w |
| $\Delta^9$ THC | NMT 0.15% w/w |
| CBD-C4 | NMT 0.5% w/w |

>—greater than

NMT—not more than

Preparation of Botanically Dervived Purified CBD

The following describes the production of the botanically derived purified CBD which comprises greater than or equal to 98% w/w CBD and less than or equal to other cannabinoids was used in the open label, expanded-access program described in Example 1 below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD w/w, typically greater than 98% w/w.

The *Cannabis sativa* L. plants are grown, harvested, and processed to produce a botanical extract (intermediate) and then purified by crystallization to yield the CBD (botanically derived purified CBD).

The plant starting material is referred to as Botanical Raw Material (BRM); the botanical extract is the intermediate; and the active pharmaceutical ingredient (API) is CBD, the drug substance.

All parts of the process are controlled by specifications. The botanical raw material specification is described in Table B and the CBD API is described in Table C.

TABLE B

| CBD botanical raw material specification | | |
| --- | --- | --- |
| Test | Method | Specification |
| Identification: | | |
| A | Visual | Complies |
| B | TLC | Corresponds to standard (for CBD & CBDA) |
| C | HPLC/UV | Positive for CBDA |
| Assay: | In-house | NLT 90% of assayed |
| CBDA + CBD | (HPLC/UV) | cannabinoids by peak area |
| Loss on Drying | Ph. Eur. | NMT 15% |
| Aflatoxin | UKAS method | NMT 4 ppb |
| Microbial: | Ph. Eur. | |
| TVC | | NMT $10^7$ cfu/g |

TABLE B-continued

| | | |
|---|---|---|
| CBD botanical raw material specification | | |
| Test | Method | Specification |
| Fungi | | NMT$10^5$ cfu/g |
| *E. coli* | | NMT$10^2$ cfu/g |
| Foreign Matter: | Ph. Eur. | NMT 2% |
| Residual Herbicides and Pesticides | Ph. Eur. | Complies |

TABLE C

| | | |
|---|---|---|
| Specification of an exemplary botanically derived purified CBD preparation | | |
| Test | Test Method | Limits |
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| CBDA | HPLC-UV | NMT 0.15% w/w |
| CBDV | | 0.2-1.0% w/w |
| THC | | 0.01-0.1% w/w |
| CBD-C4 | | 0.3-0.5% w/w |
| Residual Solvents: | | |
| Alkane | GC | NMT 0.5% w/w |
| Ethanol | | NMT 0.5% w/w |
| Residual Water | Karl Fischer | NMT 1.0% w/w |

The purity of the botanically derived purified CBD preparation was greater than or equal to 98%. The botanically derived purified CBD includes THC and other cannabinoids, e.g., CBDA, CBDV, CBD-C1, and CBD-C4.

In some embodiments, the CBD preparation comprises not more than 0.15% THC based on total amount of cannabinoid in the preparation. In some embodiments, the CBD preparation comprises about 0.01% to about 0.1% THC based on total amount of cannabinoid in the preparation. In some embodiments, the CBD preparation comprises about 0.02% to about 0.05% THC based on total amount of cannabinoid in the preparation.

In some embodiments, the CBD preparation comprises about 0.2% to about 1.0% CBDV based on total amount of cannabinoid in the preparation. In some embodiments, the CBD preparation comprises about 0.2% to about 0.8% CBDV based on total amount of cannabinoid in the preparation.

In some embodiments, the CBD preparation comprises about 0.3% to about 0.5% CBD-C4 based on total amount of cannabinoid in the preparation. In some embodiments, the CBD preparation comprises about 0.3% to about 0.4% CBD-C4 based on total amount of cannabinoid in the preparation.

In some embodiments, the CBD preparation comprises about 0.1% to about 0.15% CBD-C1 based on total amount of cannabinoid in the preparation.

Distinct chemotypes of the *Cannabis sativa* L. plant have been produced to maximize the output of the specific chemical constituents, the cannabinoids. Certain chemovars produce predominantly CBD. Only the (−)-trans isomer of CBD is believed to occur naturally. During purification, the stereochemistry of CBD is not affected.

Production of CBD Botanical Drug Substance

An overview of the steps to produce a botanical extract, the intermediate, are as follows:

a) Growing b) Direct drying c) Decarboxylation d) Extraction—using liquid $CO_2$ e) Winterization using ethanol f) Filtration g) Evaporation High CBD chemovars were grown, harvested, dried, baled and stored in a dry room until required. The botanical raw material (BRM) was finely chopped using an Apex mill fitted with a 1 mm screen. The milled BRM was stored in a freezer prior to extraction.

Decarboxylation of CBDA to CBD was carried out using heat. BRM was decarboxylated at 115° C. for 60 minutes.

Extraction was performed using liquid $CO_2$ to produce botanical drug substance (BDS), which was then crystalized to produce the test material. The crude CBD BDS was winterized to refine the extract under standard conditions (2 volumes of ethanol at −20° C. for approximately 50 hours).

The precipitated waxes were removed by filtration and the solvent was removed to yield the BDS.

Production of Botanically Derived Purified CBD Preparation

The manufacturing steps to produce the botanically derived purified CBD preparation from BDS were as follows:

a) Crystallization using $C_5$-$C_{12}$ straight chain or branched alkane b) Filtration c) Vacuum Drying The BDS produced using the methodology above was dispersed in $C_5$-$C_{12}$ straight chain or branched alkane. The mixture was manually agitated to break up any lumps and the sealed container then placed in a freezer for approximately 48 hours. The crystals were isolated via vacuum filtration, washed with aliquots of cold $C_5$-$C_{12}$ straight chain or branched alkane, and dried under a vacuum of <10 mb at a temperature of 60° C. until dry. The botanically derived purified CBD preparation was stored in a freezer at −20° C. in a pharmaceutical grade stainless steel container, with FDA food grade approved silicone seal and clamps.

Physicochemical Properties of the Botanically Derived Purified CBD

The botanically derived purified CBD used in the clinical trial described in the invention comprises greater than or equal to 98% (w/w) CBD and less than or equal to 2% (w/w) of other cannabinoids. The other cannabinoids present are THC at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w).

The botanically derived purified CBD used additionally comprises a mixture of both trans-THC and cis-THC. It was found that the ratio of the trans-THC to cis-THC is altered and can be controlled by the processing and purification process, ranging from 3.3:1 (trans-THC:cis-THC) in its unrefined decarboxylated state to 0.8:1 (trans-THC:cis-THC) when highly purified.

Furthermore, the cis-THC found in botanically derived purified CBD is present as a mixture of both the (+)-cis-THC and the (−)-cis-THC isoforms.

Clearly a CBD preparation could be produced synthetically by producing a composition with duplicate components.

Example 1 below describes the use of a botanically derived purified CBD in an open label, expanded-access program to investigate the clinical efficacy and safety of purified pharmaceutical cannabidiol formulation (CBD) in the treatment of patients diagnosed with Rett syndrome.

Example 1: Clinical Efficacy and Safety of Purified Pharmaceutical Cannabidiol (Cbd) in the Treatment of Patients Diagnosed with Rett Syndrome Study Design Subjects were required to be on one or more AEDs at stable doses for a minimum of two weeks prior to baseline and to have stable vagus nerve stimulation (VNS) settings and ketogenic diet ratios for a minimum of four weeks prior to baseline.

Patients were administered botanically derived purified CBD in a 100 mg/mL sesame oil-based solution which was titrated to an initial dose of between 5 and 25 milligrams per kilogram per day (mg/kg/day) in two divided doses. Doses were then increased weekly by 5 mg/kg/day to a goal of 25 mg/kg/day where required.

A maximum dose of 50 mg/kg/day could be utilised for patients who were tolerating the medication but had not achieved seizure control; these patients had further weekly titration by 5 mg/kg/day.

There were three patients in this study, and each received CBD for various durations of time. Modifications were made to concomitant AEDs as per clinical indication.

Seizure frequency, intensity, and duration were recorded by caregivers in a diary during a baseline period of at least 28 days. Changes in seizure frequency relative to baseline were calculated after at least 2 weeks and at defined time-points of treatment.

Statistical Methods:

Patients may be defined as responders if they had more than 50% reduction in seizure frequency compared to baseline. The percent change in seizure frequency was calculated as follows:

$$\% \text{ change seizure frequency} = \frac{(\text{weekly seizure frequency time interval}) - (\text{weekly seizure frequency Baseline})}{(\text{weekly seizure frequency Baseline})} \times 100$$

The percent change of seizure frequency may be calculated for any time interval where seizure number has been recorded. For the purpose of this example the percent change of seizure frequency for the end of the treatment period was calculated as follows:

$$\% \text{ reduction seizure frequency} = \frac{((\text{weekly seizure frequency Baseline}) - (\text{weekly seizure frequency End}))}{(\text{weekly seizure frequency Baseline})} \times 100$$

Results

Patient Description

The three patients enrolled in the open label; expanded-access program were diagnosed with Rett syndrome. These patients experienced a range of different seizure types including tonic, tonic-clonic, absence and focal seizures with impairment.

The age of patients ranged from 6-9 years, all three were female as detailed in Table 1 below.

TABLE 1

Patient demographics, seizure type and concomitant medication

| Patient Number | Age (years) | Sex | Seizure types | Concomitant AEDs |
|---|---|---|---|---|
| 1 | 9.01 | F | Tonic Tonic-clonic | PMP, VPA, ZNS |
| 2 | 8.69 | F | Tonic Absence Focal with impairment | CLZ, DZP, LEV, CLB, ZNS |
| 3 | 6.67 | F | Tonic Tonic-clonic Absence | CLB, LEV, VPA, ZNS |

PMP = perampanel,
VPA = valproic acid,
ZNS = zonisamide,
CLZ = clonazepam,
DZP = diazepam,
LEV = levetiracetam,
CLB = clobazam Study Medication and Concomitant Medications Patients on the study were titrated up to various doses of CBD, all patients were titrated up to at least 21.3 mg/kg/day.

Patients were taking an average of four AEDs.

Clinical Changes

Tables 2A-2C illustrate the seizure frequency for each patient as well as the dose of CBD given.

TABLE 2A

| Seizure frequency data for Patient 1 Patient 1 | | | |
| --- | --- | --- | --- |
| | Seizure Type | | Dose CBD |
| Time | Tonic | Tonic-clonic | (mg/kg/day) |
| Baseline | 22.4 | 10.0 | — |
| 2 weeks | 22.0 | 26.0 | 5.0 |
| 4 weeks | 38.0 | 21.4 | 10.0 |
| 8 weeks | 28.0 | 14.0 | 20.0 |
| 12 weeks | 28.0 | 12.0 | 25.0 |
| 16 weeks | 14.0 | 22.0 | 15.0 |
| 24 weeks | 8.0 | 12.0 | 15.0 |
| 36 weeks | 20.0 | 20.0 | 15.0 |

Patient 1 was treated for 36 weeks and experienced a 10.7% reduction in tonic seizures over the treatment period.

TABLE 2B

| Seizure frequency data for Patient 2 Patient 2 | | | | |
| --- | --- | --- | --- | --- |
| | Seizure Type | | | |
| Time | Tonic | Absence | Focal with impairment | Dose CBD (mg/kg/day) |
| Baseline | 5.6 | 0 | 3.2 | — |
| 8 weeks | 3.0 | 1.0 | 0 | 20.0 |
| 12 weeks | 1.6 | 0 | 0 | 20.0 |
| 16 weeks | 2.0 | 0 | 0 | 20.0 |
| 24 weeks | 0.4 | 0.8 | 0 | 20.0 |
| 36 weeks | 0.4 | 0.4 | 0 | 20.0 |
| 48 weeks | 0.8 | 0 | 0 | 20.0 |
| 60 weeks | 1.4 | 0 | 0 | 20.0 |
| 72 weeks | 0.4 | 0.4 | 0 | 21.3 |
| 84 weeks | 0.4 | 0.4 | 0 | 20.0 |

Patient 2 was treated for 84 weeks and experienced a 92.9% reduction in tonic seizures and a 100% reduction in focal seizures with impairment over the treatment period.

TABLE 2C

| Seizure frequency data for Patient 3 Patient 3 | | | | |
| --- | --- | --- | --- | --- |
| | Seizure Type | | | Dose CBD |
| Time | Tonic | Tonic-clonic | Absence | (mg/kg/day) |
| Baseline | 16.0 | 4.0 | 8.0 | — |
| 4 weeks | 2.0 | 4.0 | 1.0 | 25.0 |
| 12 weeks | 1.0 | 4.0 | 0 | 25.0 |
| 16 weeks | 4.0 | 6.0 | 0 | 25.0 |
| 24 weeks | 0 | 8.0 | 4.0 | 25.0 |
| 36 weeks | 4.0 | 6.0 | 1.0 | 25.0 |

Patient 2 was treated for 36 weeks and experienced a 75% reduction in tonic seizures and an 87.5% reduction in absence seizures over the treatment period.

Overall, patients reported reductions of 10.7-100.0% in seizures over the period of treatment with CBD.

CBD was effective in reducing the frequency of the following seizure types: tonic, absence and focal seizures with impairment. Significantly, one patient became seizure free of focal seizures with impairment (patent 2). All three patients suffered from tonic seizures and all three experienced a reduction in their tonic seizures of between 11-93%.

CONCLUSIONS

These data indicate that CBD was able to significantly reduce the number of seizures associated with Rett syndrome. Clearly the treatment is of significant benefit in this difficult to treat epilepsy syndrome given the high responder rate experienced in all three patients.

In conclusion, this study signifies the use of CBD for treatment of seizures associated with Rett syndrome. Seizure types include tonic, tonic-clonic, absence and focal seizures with impairment for which seizure frequency rates decreased by significant rates, by 11-100.0%.

REFERENCES 1. https://clinicaltrials.gov/ct2/show/ NCT03848832?term=cannabidiol&cond=Rett+Syndrome Accessed: 10 Jul. 2020.
2. Vigli et al. (2018) "Chronic Treatment With the Phytocannabinoid Cannabidivarin (CBDV) Rescues Behavioural Alterations and Brain Atrophy in a Mouse Model of Rett Syndrome" Neuropharmacology
3. Way (2019) "How one canna-mom treats her daughter's Rett syndrome with *cannabis.*" *Cannabis* Now https:// cannabisnow.com/how-one-canna-mom-treats-her-daughters-rett-syndrome-with-*cannabis/*
4. Mouro et al. (2019) "From cannabinoids and neurosteroids to statins and the ketogenic diet: New therapeutic avenues in Rett syndrome." Frontiers in Neuroscience, vol. 13, Article 680; pages 1-22

The invention claimed is:

1. A method for treating seizures associated with Rett syndrome comprising administering a cannabidiol (CBD) preparation, wherein the seizures associated with Rett syndrome are tonic, tonic-clonic, absence, and focal seizures with impairment.

2. The method of claim 1, wherein the CBD preparation comprises greater than 95% (w/w) CBD and not more than 0.15% (w/w) tetrahydrocannabinol (THC).

3. The method of claim 1, wherein the CBD preparation comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC.

4. The method of claim 1, wherein the CBD preparation is used in combination with one or more concomitant anti-epileptic drugs (AED).

5. The method of claim 4, wherein the one or more AED is selected from the group consisting of: clobazam, levetiracetam, zonisamide, valproic acid, perampanel, clonazepam and diazepam.

6. The method of claim 1, wherein the CBD that is present is isolated from *cannabis* plant material.

7. The method of claim 1, wherein at least a portion of at least one of the cannabinoids present in the CBD preparation is isolated from *cannabis* plant material.

8. The method of claim 1, wherein the CBD is present as a synthetic preparation.

9. The method of claim 8, wherein at least a portion of at least one of the cannabinoids present in the CBD preparation is prepared synthetically.

10. The method of claim 1, wherein the dose of CBD is greater than 5 mg/kg/day.

11. The method of claim 1, wherein the dose of CBD is 20 mg/kg/day.

12. The method of claim 1, wherein the dose of CBD is 25 mg/kg/day.

13. The method of claim 1, wherein the dose of CBD is 50 mg/kg/day.

* * * * *